US011786601B2

(12) United States Patent
Legler et al.

(10) Patent No.: US 11,786,601 B2
(45) Date of Patent: Oct. 17, 2023

(54) PEGYLATED CAPSULE-DEGRADING ENZYME FOR THE TREATMENT OF ANTHRAX

(71) Applicant: The Government of the United States of America, as represented by the Secretary of the Navy, Arlington, VA (US)

(72) Inventors: Patricia M. Legler, Derwood, MD (US); Arthur M. Friedlander, Frederick, MD (US); Jaimee R. Compton, Washington, DC (US)

(73) Assignee: The Government of the United States of America, as represented by the Secretary of the Navy, Arlington, VA (US)

( * ) Notice: Subject to any disclaimer, the term of this patent is extended or adjusted under 35 U.S.C. 154(b) by 0 days.

(21) Appl. No.: 17/577,893

(22) Filed: Jan. 18, 2022

(65) Prior Publication Data

US 2022/0233703 A1 Jul. 28, 2022

Related U.S. Application Data

(60) Provisional application No. 63/140,455, filed on Jan. 22, 2021.

(51) Int. Cl.
*A61K 47/60* (2017.01)
*A61K 38/45* (2006.01)

(52) U.S. Cl.
CPC .............. *A61K 47/60* (2017.08); *A61K 38/45* (2013.01)

(58) Field of Classification Search
CPC ................................ A61K 47/60; A61K 38/45
See application file for complete search history.

(56) References Cited

U.S. PATENT DOCUMENTS

2010/0226906 A1 9/2010 Friedlander et al.

OTHER PUBLICATIONS

Czajkowsky, Daniel M. et al. "Fc-fusion Proteins: New Developments and Future Perspectives." EMBO molecular medicine 4.10 (2012): 1015-1028. Web (Year: 2012).*

Roberts, M.J., M.D. Bentley, and J.M. Harris. "Chemistry for Peptide and Protein PEGylation." Advanced drug delivery reviews 64 (2012): 116-127. Web. (Year: 2012).*

Luo, Zhiting et al. "Microbial Synthesis of Poly-γ-Glutamic Acid: Current Progress, Challenges, and Future Perspectives." Biotechnology for biofuels 9.1 (2016): 134-134. Web. (Year: 2016).*

Wu et al., J. Biol. Chem. 286 (37), 32586-32592 (2011).

* cited by examiner

*Primary Examiner* — Louise W Humphrey
*Assistant Examiner* — John Paul Selwanes
(74) *Attorney, Agent, or Firm* — US Naval Research Laboratory; Roy Roberts

(57) ABSTRACT

A pegylated, circularly permuted construct of the CapD enzyme (a gamma glutamyl transferase enzyme acting as a hydrolase specific to poly-γ-D-glutamic acid) is used to treat anthrax and other bacterial infections, including but not limited to infection with strains that are resistant to available antibiotics.

2 Claims, 1 Drawing Sheet

Specification includes a Sequence Listing.

PEGYLATED CAPSULE-DEGRADING ENZYME FOR THE TREATMENT OF ANTHRAX

CROSS-REFERENCE TO RELATED APPLICATIONS

This application claims the benefit of U.S. Provisional Patent Application No. 63/140,455 filed on Jan. 22, 2021, which incorporated herein by reference in its entirety.

BACKGROUND

*Bacillus anthrucis*, the causative agent of anthrax, has been known to develop antibiotic resistance. However, the bacteria relies on a capsule of poly-γ-D-glutamic acid to shield the bacterium from killing by phagocytic cells (such as in a human host). This polymer is unique to bacteria and is not present in humans; it serves to shield the bacterium from phagocytic cells in a human host. The anti-phagocytic property of the capsule is the primary mechanism of immune cell evasion utilized by *B. anthracis* and is critical for virulence.

CapD is a gamma glutamyl transferase enzyme acting as a protease specific to poly-γ-D-glutamic acid. CapD is normally autocatalytic and forms a heterodimer consisting of 35 kDa and 15 kDa polypeptides. When added exogenously to encapsulated bacilli, the enzyme efficiently degrades the capsule, essentially removing it from the surface of the bacilli, allowing neutrophils to kill the unencapsulated bacteria.

A need exists for novel treatments effective against anthrax infection, particularly in the event of infection with strains that are resistant to available antibiotics.

BRIEF SUMMARY

In one embodiment, a purified and isolated protein is a pegylated, circularly permuted construct of the CapD enzyme having activity against poly-γ-D-glutamic acid and/or poly-γ-DL-glutamic acid, and optionally further comprising a Fc domain fused thereto.

DETAILED DESCRIPTION

Definitions

Figure 1A:
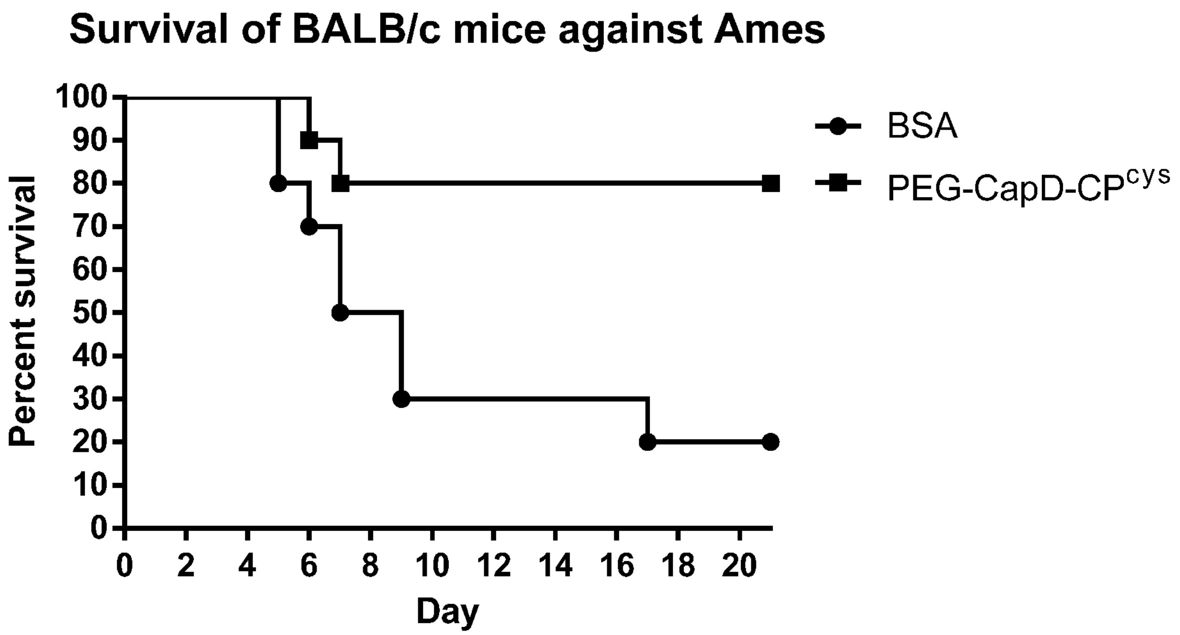
FIGS. 1A and 1B show data on survival of mice exposed to *B. anthracis* spores and treated with of CapD-CP$^{S334C}$ or control.

Before describing the present invention in detail, it is to be understood that the terminology used in the specification is for the purpose of describing particular embodiments, and is not necessarily intended to be limiting. Although many methods, structures and materials similar, modified, or equivalent to those described herein can be used in the practice of the present invention without undue experimentation, the preferred methods, structures and materials are described herein. In describing and claiming the present invention, the following terminology will be used in accordance with the definitions set out below.

As used herein, the singular forms “a”, “an,” and “the” do not preclude plural referents, unless the content clearly dictates otherwise.

As used herein, the term “and/or” includes any and all combinations of one or more of the associated listed items.

As used herein, the term “about” when used in conjunction with a stated numerical value or range denotes somewhat more or somewhat less than the stated value or range, to within a range of ±10% of that stated.

Overview

The concept of combatting anthrax with the native form of CapD enzyme was discussed in U.S. Patent Application Publication 2010/0226906. This native enzyme has SEQ ID NO: 1 which is as follows:

```
MNSFKWGKKIILFCLIVSLMGGIGVSCSFNKIKDS
VKQKIDSMGDKGTYGVSASHPLAVEEGMKVLKNGG
SAVDAAIVVSYVLGVVELHASGIGGGGGMLIISKD
KETFIDYRETTPYFTGNQKPHIGVPGFVAGMEYIH
DNYGSLPMGELLQPAINYAEKGFKVDDSLTMRLDL
AKPRIYSDKLSIFYPNGEPIETGETLIQTDLARTL
KKIQKEGAKGFYEGGVARAISKTAKISLEDIKGYK
VEVRKPVKGNYMGYDVYTAPPPFSGVTLLQMLKLA
EKKEVYKDVDHTATYMSKMEEISRIAYQDRKKNLG
DPNYVNMDPNKMVSDKYISTMKNENGDALSEAEHE
STTHFVIIDRDGTVVSSTNTLSNFFGTGKYTAGFF
LNNQLQNFGSEGFNSYEPGKRSRTFMAPTVLKKDG
ETIGIGSPGGNRIPQILTPILDKYTHGKGSLQDII
NEYRFTFEKNTAYTEIQLSSEVKNELSRKGLNVKK
KVSPAFFGGVQALIKDERDNVITGAGDGRRNGTWK
SNK.
```

Described herein are modified versions of this native CapD enzyme that are especially suited to treat anthrax infection. Of particular value are forms of CapD having improved stability and/or improved activity.

The native, or wild-type, CapD is produced as a single polypeptide which autocatalytically cleaves itself to produce a new N-terminal residue. As previously described in *J. Biol. Chem. Vol* 286(37):32586-32592 (2011), the circularly permuted construct of CapD (CapD-CP) does not require this cleavage and also exhibits enhanced stability as compared to the wild-type.

Stability was further improved by functionalizing the enzyme with polyethylene glycol (PEG), termed pegylation. Such treatment may also desirably reduce immunogenicity of the enzyme.

Pegylation of enzymes often results in reduction of enzyme activity by hindering substrate binding. The present inventors found that the S334C mutation allowed pegylation while retaining activity. This CapD-CP$^{S334C}$ protein has SEQ ID NO: 2 which is as follows:

```
MTTHFVIIDRDGTVVSSTNTLSNFFGTGKYTAGFF
LNNQLQNFGSEGFNSYEPGKRSRTFMAPTVLKKDG
ETIGIGSPGGNRIPQILTPILDKYTHGKGSLQDII
NEYRFTFEKNTAYTEIQLSSEVKNELSRKGLNVKK
```

-continued

```
KVSPAFFGGVQALIKDERDNVITGAGDGRRNGTWK

SGGSGTYGVSASHPLAVEEGMKVLKNGGSAVDAAI

VVSYVLGVVELHASGIGGGGGMLIISKDKETFIDY

RETTPYFTGNQKPHIGVPGFVAGMEYIHDNYGSLP

MGELLQPAINYAEKGFKVDDSLTMRLDLAKPRIYS

DKLSIFYPNGEPIETGETLIQTDLARTLKKIQKEG

AKGFYEGGVARAISKTAKISLEDIKGYKVEVRKPV

KGNYMGYDVYTAPPPFSGVTLLQMLKLAEKKEVYK

DVDHTATYMSKMEEISRIAYQDRKKNLGDPNYVNM

DPNKMVSDKYICTMKNENGDALSEAEHESGSTENL

YFQSGALEHHHHHH.
```

As detailed below, this protein was very effective in treating anthrax in an animal model.

The above protein includes a C-terminal polyhistidine tag to assist purification. An additional protein was developed with a cleavage site for Factor Xa integrated immediately prior to the tag in order to allow for its removal. This CapDcp S334C Clone XAI has SEQ ID NO: 3 which is as follows:

```
MTTHFVIIDRDGTVVSSTNTLSNFFGTGKYTAGFF

LNNQLQNFGSEGFNSYEPGKRSRTFMAPTVLKKDG

ETIGIGSPGGNRIPQILTPILDKYTHGKGSLQDII

NEYRFTFEKNTAYTEIQLSSEVKNELSRKGLNVKK

KVSPAFFGGVQALIKDERDNVITGAGDGRRNGTWK

SGGSGTYGVSASHPLAVEEGMKVLKNGGSAVDAAI

VVSYVLGVVELHASGIGGGGGMLIISKDKETFIDY

RETTPYFTGNQKPHIGVPGFVAGMEYIHDNYGSLP

MGELLQPAINYAEKGFKVDDSLTMRLDLAKPRIYS

DKLSIFYPNGEPIETGETLIQTDLARTLKKIQKEG

AKGFYEGGVARAISKTAKISLEDIKGYKVEVRKPV

KGNYMGYDVYTAPPPFSGVTLLQMLKLAEKKEVYK

DVDHTATYMSKMEEISRIAYQDRKKNLGDPNYVNM

DPNKMVSDKYICTMKNENGDALSEAEHESIEGRVS

LEHHHHHHH.
```

The fusion of the Fc domain of an antibody to a therapeutic enzyme or protein can improve the in vivo circulation time of the enzyme and potentially reduce the amount of enzyme needed for protection. These immunotherapeutics can be recycled via the neonatal Fc-receptor (FcRn) in adults. However, because they are endocytosed during recycling these proteins are exposed to a low-pH environment where they can irreversibly denature and lose their enzymatic activity. It was found that pegylation of CapD prevents irreversible acid-denaturation of the enzyme. The fusion of the Fc-domain also unexpectedly imparted acid stability.

In further embodiments, a fusion protein of the immunoglobulin Fc domain to the S334C CapD-CP was generated to generate a homodimeric pegylated immunotherapeutic. The fusion of the Fc-domain increases the half-life of the enzyme in vivo, and also enhances the avidity of the enzyme to its polymeric substrate and improve clearance of low levels of bacteria. One such protein is Fc-CapD-CP w/Factor Xa site CF2A having SEQ ID NO: 4 which is as follows:

```
MTTHFVIIDRDGTVVSSTNTLSNFFGTGKYTAGFF

LNNQLQNFGSEGFNSYEPGKRSRTFMAPTVLKKDG

ETIGIGSPGGNRIPQILTPILDKYTHGKGSLQDII

NEYRFTFEKNTAYTEIQLSSEVKNELSRKGLNVKK

KVSPAFFGGVQALIKDERDNVITGAGDGRRNGTWK

SGGSGTYGVSASHPLAVEEGMKVLKNGGSAVDAAI

VVSYVLGVVELHASGIGGGGGMLIISKDKETFIDY

RETTPYFTGNQKPHIGVPGFVAGMEYIHDNYGSLP

MGELLQPAINYAEKGFKVDDSLTMRLDLAKPRIYS

DKLSIFYPNGEPIETGETLIQTDLARTLKKIQKEG

AKGFYEGGVARAISKTAKISLEDIKGYKVEVRKPV

KGNYMGYDVYTAPPPFSGVTLLQMLKLAEKKEVYK

DVDHTATYMSKMEEISRIAYQDRKKNLGDPNYVNM

DPNKMVSDKYICTMKNENGDALSEAEHESGSGAKK

IVPRDCGCKPCICTVPEVSSVFIFPPKPKDVLTIT

LTPKVTCVVVDISKDDPEVQFSWFVDDVEVHTAQT

QPREEQFNSTFRSVSELPIMHQDWLNGKEFKCRVN

SAAFPAPIEKTISKTKGRPKAPQVYTIPPPKEQMA

KDKVSLTCMITDFFPEDITVEWQWNGQPAENYKNT

QPIMDTDGSYFVYSKLNVQKSNWEAGNTFTCSVLH

EGLHNHHTEKSLSHSPGKLGIEGRLEHHHHHH.
```

Another embodiment based on the above is termed LCF7 and produced higher yields than the CF2A variant which was prone to aggregation. This LCF7 protein has SEQ ID NO: 5 which is as follows:

```
MTTHFVIIDRDGTVVSSTNTLSNFFGTGKYTAGFF

LNNQLQNFGSEGFNSYEPGKRSRTFMAPTVLKKDG

ETIGIGSPGGNRIPQILTPILDKYTHGKGSLQDII

NEYRFTFEKNTAYTEIQLSSEVKNELSRKGLNVKK

KVSPAFFGGVQALIKDERDNVITGAGDGRRNGTWK

SGGSGTYGVSASHPLAVEEGMKVLKNGGSAVDAAI

VVSYVLGVVELHASGIGGGGGMLIISKDKETFIDY

RETTPYFTGNQKPHIGVPGFVAGMEYIHDNYGSLP

MGELLQPAINYAEKGFKVDDSLTMRLDLAKPRIYS

DKLSIFYPNGEPIETGETLIQTDLARTLKKIQKEG

AKGFYEGGVARAISKTAKISLEDIKGYKVEVRKPV

KGNYMGYDVYTAPPPFSGVTLLQMLKLAEKKEVYK
```

-continued

```
DVDHTATYMSKMEEISRIAYQDRKKNLGDPNYVNM

DPNKMVSDKYICTMKNENGDALSEAEHESGSGAKK

IVPRDCGCKPCICTVPEVSSVFIFPPKPKDVLTIT

LTPKVTCVVVDISKDDPEVQFSWFVDDVEVHTAQT

QPREEQFNSTFRSVSELPIMHQDWLNGKEFKCRVN

SAAFPAPIEKTISKTKGRPKAPQVYTIPPPKEQMA

KDKVSLTCMITDFFPEDITVEWQWNGQPAENYKNT

QPIMDTDGSYFVYSKLNVQKSNWEAGNTFTCSVLH

EGLHNHHTEKSLSHSPGKLGIEGRGSSGLEHHHHH

H.
```

Fc-fusions are homodimeric and the poly-D-glutamate (PDGA) substrate is polymeric and anchored to the surface of the bacterial peptidoglycan. Avidity will affect the association rate of a homodimeric enzyme to its substrate, i.e., once one enzyme binds to the PDGA polymer, the second enzyme will bind more quickly. Thus, the increased avidity of the CapD Fc-fusion enhances the clearance of very low levels of bacteria in the blood.

Examples

Proteins were produced in *E. coli* and purified using standard techniques. In the case of pegylated proteins, pegylation was performed using (methyl-$PEG_{12}$)$_3$-$PEG_4$-maleimide with a molecular weight of 2360.75 g/mol or with PEG-maleimide with a molecular weight of ~2000 g/mol prior to purification.

Figure 1B:
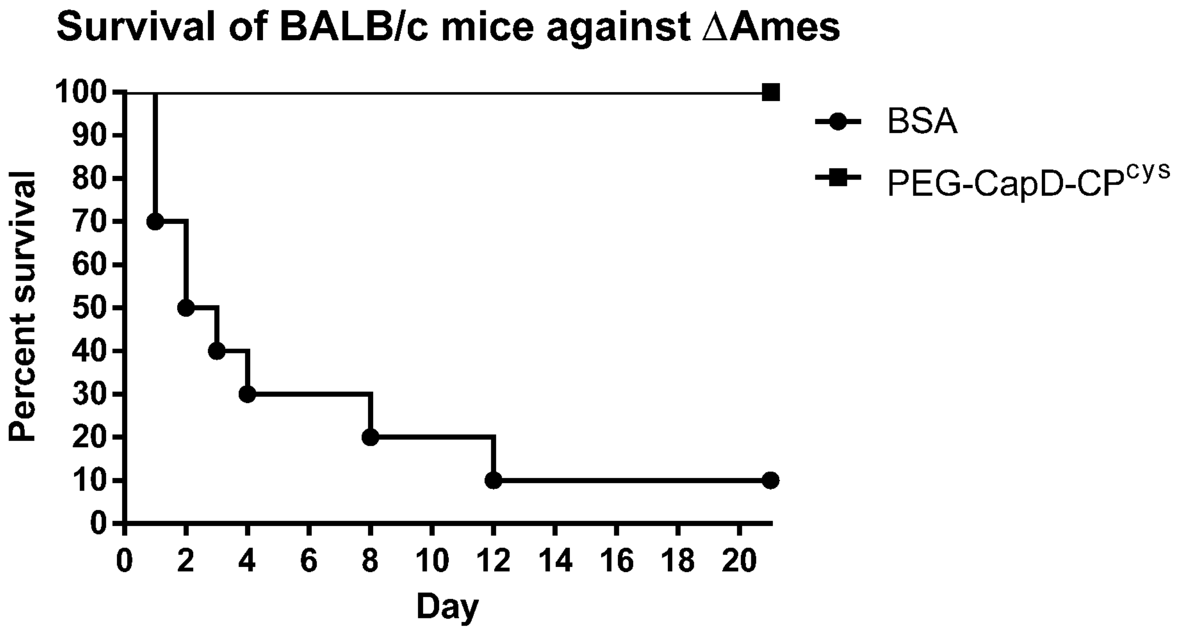

Mice were exposed to five times the $LD_{50}$ of *B. anthracis* Ames spores and then treated by intraperitoneal injection of 40 mg/kg of CapD-$CP^{S334C}$ delivered 24 hours post-exposure every 8 hours for 2 days (for a total of six injections), or control injections of bovine serum albumin (BSA). The pegylated protein was protective in vim against 5×$LD_{50}$ of *B. anthracis* Ames spore challenge (80% survival) as seen in FIG. 1A. Similar results were seen in mice exposed to the ΔAmes variant of anthrax as shown in FIG. 1B.

Further Embodiments

The depolymerases described herein can be produced in hosts besides *E. coli*. Pegylation can be done at sites other than those described and various forms of PEG-maleimides can be employed, for example single chain and branched chain forms, and those having different lengths.

It is contemplated that delivery of the enzyme to a subject known or suspected of having an anthrax infection, or of having been exposed to anthrax, might be effective to ameliorate the disease. Thus, a medicament is contemplated comprising the enzyme in conjunction with a pharmaceutically-acceptable carrier. In further embodiments, treatment includes providing not just the enzyme but one or more antibiotics.

The capsule depolymerases fused to Fc-domains described herein can be used to treat *Bacillus anthracis* (anthrax), *Staphylococcus epidermidis* and other illnesses involving bacterial organisms having a capsule, including preferably those having a capsule which in part or in whole contains poly-γ-D-glutamic acid or mixed polymers of poly-γ-D/L-glutamic acid. Other types of capsule depolymerases, besides CapD, and including pegylated and/or Fc fusion forms of such enzymes, might be used on similarly against bacterial having capsules comprising substrates of these depolymerases.

In some preferable embodiments, the above-noted bacteria comprise, consist of, consist essentially of, or are, antibiotic resistant strains. Without wishing to be bound to a particular theory, it is believed that the capsule depolymerases fused to Fc-domains can remove the capsule from the bacterial surface making the bacterium susceptible to or more susceptible to killing by immune cells. Accordingly, the treatment is useful for a variety of illnesses caused by bacterial infections, including by way of illustration, but not limitation, septicemia and infections of deep tissue and prosthetic devices.

Administration of the therapy could be performed orally or parenterally, or intravenously in amounts sufficient to enable the enzymes to degrade the organism's capsule. The administered protein can be in pure form, a fragment of the peptide, or a modified form of the peptide retaining enzymatic activity. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine, and derivatives thereof. Alternative protein modification techniques may be used e.g., $NH_2$-acetylation or COOH-terminal amidation, to provide additional means for coupling or fusing the peptide to another protein or peptide molecule or to a support.

Pharmaceutically acceptable carrier include carriers that do not themselves induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, and inactive virus particles. The carrier can comprise, consist of, consist essentially of, or be a saline solution, dextrose, albumin, a serum, or any of those disclosed in U.S. Pub. Nos.: 2008/0138408; 2009/0061003; 2009/0123530; 2010/0303901; 2012/0034198; and 2016/0008290 and U.S. Pat. Nos. 6,992,066; 5,785,973; 7,485,294; 8,088,734; 8,753,645; 8,808,733; and 8,858,998.

The compositions typically will contain pharmaceutically acceptable vehicles, such as water, saline, glycerol, ethanol, etc. Additionally, auxiliary substances, such as wetting or emulsifying agents, pH buffering substances, preservatives, and the like, may be included in such vehicles.

Typically, the compositions are prepared as injectables, either as liquid solutions or suspensions; solid forms suitable for solution in, or suspension in, liquid vehicles prior to injection may also be prepared. The preparation also may be emulsified or encapsulated in liposomes. Solutions for infusion or injection may be prepared in a conventional manner, e.g. with the addition of preservatives such as p-hydroxybenzoates or stabilizers such as alkali metal salts of ethylenediamine tetraacetic acid, which may then be transferred into fusion vessels, injection vials or ampules. Alternatively, the compound for injection may be lyophilized either with or without the other ingredients and be solubilized in a buffered solution or distilled water, as appropriate, at the time of use. Non-aqueous vehicles such as fixed oils and ethyl oleate are also useful herein.

In cases where intramuscular injection is the mode of administration, an isotonic formulation can be used. Generally, additives for isotonicity can include sodium chloride, dextrose, mannitol, sorbitol and lactose. In some cases isotonic solutions such as phosphate buffered saline are preferred. Stabilizers include glycerol, gelatin and albumin which may be included in the formulation. In some embodiments, a vasoconstriction agent is added to the formulation.

Additional pharmaceutical methods may be employed to control the duration of action. Controlled release preparations may be achieved through the use of polymers to complex or absorb the compounds. The controlled delivery may be exercised by selecting appropriate macromolecules (for example polyesters, polyamino acids, polyvinyl, pyrrolidone, ethylenevinylacetate, methylcellulose, carboxymethylcellulose, or protamine sulfate) and the concentration of macromolecules as well as the method of incorporation in order to control release. Another possible method to control the duration of action by controlled release preparations is to incorporate the compounds of the present invention into particles of a polymeric material such as polyesters, polyamino acids, hydrogels, polylactic acid or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions.

Administration of the compounds disclosed herein may be carried out by any suitable means, including parenteral injection (such as intravenous intraperitoneal, subcutaneous, or intramuscular injection), orally, or by topical application of the enzymes (typically carried in a pharmaceutical formulation) to an airway surface. Topical application to an airway surface can be carried out by intranasal administration (e.g., by use of dropper, swab, or inhaler which deposits a pharmaceutical formulation intranasally). Topical application to an airway surface can also be carried out by inhalation administration, such as by creating respirable particles of a pharmaceutical formulation (including both solid particles and liquid particles) containing the compounds as an aerosol suspension, and then causing the subject to inhale the respirable particles. Methods and apparatus for administering respirable particles of pharmaceutical formulations can be employed and include those disclosed in U.S. Pub. Nos.: 2006/0025326; 2010/0119587; and 2017/0314008; U.S. Pat. Nos. 6,017,528; 6,153,224; 6,221,338; 6,254,854; 6,893,635; 7,947,308; 8,137,657; and 9,249,424. Oral administration may be in the form of an ingestible liquid or solid formulation.

The treatment may be given to a subject in need of treatment and may include, but are not limited to, humans or ruminants, such as sheep and cows.

In order to accelerate treatment of the infection, the therapeutic agent may further include at least one complementary agent which can also potentiate the bactericidal activity of the enzyme. The complementary agent can be penicillin, ciprofloxacin, vancomycin, synthetic penicillins, bacitracin, methicillin, cephalosporin, polymyxin, cefaclor. Cefadroxil, cefamandole nafate, cefazolin, cefixime, cefmetazole, cefonioid, cefoperzone, ceforanide, cefotanme, cefotaxime, cefotetan, cefoxitin, cefpodoxime proxetil, ceftazidine, ceftizoxime, ceftriaxone, ceftriaxone moxalactam, cefuroxime, dihydratecephalothin, moxalactam, loracarbef, mafate, chelating agents, other antibiotics and any combinations thereof in amounts which are effective to synergistically enhance the therapeutic effect of the enzyme.

The treatment may be given in a single dose schedule, or a multiple dose schedule in which a primary course of treatment may be followed with a number of separate doses, followed by other doses given at subsequent time intervals required to maintain and or reinforce the response, for example, at 1-4 days for a second dose, and if needed, a subsequent dose(s) after several days. Separate doses may include separate routes of administration, for example, oral and inhaled, intraperitoneal and intravenous, etc. Examples of suitable treatment schedules include: (i) 0, 1 day and 7 days, (ii) 0 and 7 days, and (iii) 0 and 14 days, or other schedules sufficient to elicit the desired responses, reducing disease symptoms, or reduce severity of disease. A dosing schedule can be developed based on pharmacokinetic studies to maintain an effective blood level.

In some embodiments, the method comprises administering 5 μg/kg (weight of compound/body weight), 10 μg/kg, 15 μg/kg, 20 μg/kg, 25 μg/kg, 30 μg/kg, 35 μg/kg, 40 μg/kg, 45 μg/kg, 50 μg/kg, 55 μg/kg, 60 μg/kg, 65 μg/kg, 70 μg/kg, 75 μg/kg, 80 μg/kg, 85 μg/kg, 90 μg/kg, 95 sg/kg, 100 μg/kg, 105 μg/kg, 110 μg/kg, 115 μg/kg, 120 μg/kg, 150 sg/kg, 200 μg/kg, 250 μg/kg, 300 μg/kg, 350 μg/kg, 400 μg/kg, 450 μg/kg, 500 μg/kg, 550 μg/kg, 600 μg/kg, 650 μg/kg, 700 μg/kg, 750 μg/kg, 800 μg/kg, 850 μg/kg, 900 μg/kg, 950 μg/kg, 1000 μg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 105 mg/kg, 110 mg/kg, 115 mg/kg, 120 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, or 1000 mg/kg of pegylated, circularly permuted construct of the CapD enzyme in a single dose schedule, in total from a multiple dose schedule, or in each dose of a multiple dose schedule. In some embodiments, the method comprises administering 5 μg, 10 μg, 15 μg, 20 μg, 25 μg, 30 μg, 35 μg, 40 μg, 45 μg, 50 μg, 55 μg, 60 μg, 65 μg, 70 μg, 75 μg, 80 μg, 85 μg, 90 μg, 95 μg, 100 μg, 105 μg, 110 μg, 115 μg, 120 μg, 150 μg, 200 μg, 250 μg, 300 μg, 350 μg, 400 μg, 450 μg, 500 μg, 550 μg, 600 μg, 650 μg, 700 μg, 750 μg, 800 μg, 850 μg, 900 μg, 950 μg, 1000 μg, 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of pegylated, circularly permuted construct of the CapD enzyme in a single dose schedule, in total from a multiple dose schedule, or in each dose of a multiple dose schedule. It is understood that higher doses could be administered for a localized administration and smaller doses could be administered systemically.

Kits may be useful for carrying out the present invention. In an embodiment, such kits comprise a first container holding enzymes as described herein. Kits can also comprise other containers holding solutions necessary or convenient for carrying out the invention. The container means can be made of glass, plastic or foil and can be a vial, bottle, pouch, tube, bag, etc. The kit may also contain written information, such as procedures for carrying out the present invention or analytical information, such as the amount of reagent contained in the first container means. The first container may be in secondary container, e.g. a box or a bag, along with other kit components.

Advantages

Unlike antibiotics, resistance to the enzyme treatment is unlikely to develop: this would require loss of the bacterial capsular material or damage to the capsule biosynthetic machinery. However, the capsular material is required for subversion of the host's immune responses. Thus, loss of the capsule would essentially produce the equivalent of a benign and non-virulent Sterne-like vaccine strain. If antibodies to CapD arise, these may not have negative effects in vim. CapD is an enzyme naturally present in *B. anthracis* and is foreign to humans and animals, it is thought to be anchored to the bacterial membrane. Antibodies to this cell-surface protein would bind to the pathogen that is being cleared. During infection with encapsulated pathogenic encapsulated strains of *B. anthracis* the CapD enzyme is already present in the host. CapD shows evidence of product inhibition and the anchored enzyme in the bacteria is likely inhibited by the thick capsular material above it. The recombinant forms of CapD are being added to the exterior face of the encapsulated bacteria and can freely diffuse to avoid product inhibition, this leads to a net effect of unencapsulation.

CONCLUDING REMARKS

All documents mentioned herein are hereby incorporated by reference for the purpose of disclosing and describing the particular materials and methodologies for which the document was cited.

Although the present invention has been described in connection with preferred embodiments thereof, it will be appreciated by those skilled in the art that additions, deletions, modifications, and substitutions not specifically described may be made without departing from the spirit and scope of the invention. Terminology used herein should not be construed as being "means-plus-function" language unless the term "means" is expressly used in association therewith.

What is claimed is:

1. A pegylated protein comprising SEQ ID NO: 2, SEQ ID NO: 3, SEQ ID NO: 4, or SEQ ID NO: 5.

2. A medicament comprising a pegylated protein comprising SEQ ID NO: 2, SEQ ID NO: 3, SEQ ID NO: 4, or SEQ ID NO: 5.

* * * * *

SEQUENCE LISTING

<160> NUMBER OF SEQ ID NOS: 5

<210> SEQ ID NO 1
<211> LENGTH: 528
<212> TYPE: PRT
<213> ORGANISM: Bacillus anthracis

<400> SEQUENCE: 1

Met Asn Ser Phe Lys Trp Gly Lys Lys Ile Ile Leu Phe Cys Leu Ile
1 5 10 15

Val Ser Leu Met Gly Gly Ile Gly Val Ser Cys Ser Phe Asn Lys Ile
20 25 30

Lys Asp Ser Val Lys Gln Lys Ile Asp Ser Met Gly Asp Lys Gly Thr
35 40 45

Tyr Gly Val Ser Ala Ser His Pro Leu Ala Val Glu Glu Gly Met Lys
50 55 60

Val Leu Lys Asn Gly Gly Ser Ala Val Asp Ala Ala Ile Val Val Ser
65 70 75 80

Tyr Val Leu Gly Val Val Glu Leu His Ala Ser Gly Ile Gly Gly Gly
85 90 95

Gly Gly Met Leu Ile Ile Ser Lys Asp Lys Glu Thr Phe Ile Asp Tyr
100 105 110

Arg Glu Thr Thr Pro Tyr Phe Thr Gly Asn Gln Lys Pro His Ile Gly
115 120 125

Val Pro Gly Phe Val Ala Gly Met Glu Tyr Ile His Asp Asn Tyr Gly
130 135 140

Ser Leu Pro Met Gly Glu Leu Leu Gln Pro Ala Ile Asn Tyr Ala Glu
145 150 155 160

Lys Gly Phe Lys Val Asp Asp Ser Leu Thr Met Arg Leu Asp Leu Ala
165 170 175

Lys Pro Arg Ile Tyr Ser Asp Lys Leu Ser Ile Phe Tyr Pro Asn Gly
180 185 190

Glu Pro Ile Glu Thr Gly Glu Thr Leu Ile Gln Thr Asp Leu Ala Arg
195 200 205

Thr Leu Lys Lys Ile Gln Lys Glu Gly Ala Lys Gly Phe Tyr Glu Gly
210 215 220

Gly Val Ala Arg Ala Ile Ser Lys Thr Ala Lys Ile Ser Leu Glu Asp
225 230 235 240

-continued

```
Ile Lys Gly Tyr Lys Val Glu Val Arg Lys Pro Val Lys Gly Asn Tyr
                245                 250                 255

Met Gly Tyr Asp Val Tyr Thr Ala Pro Pro Pro Phe Ser Gly Val Thr
            260                 265                 270

Leu Leu Gln Met Leu Lys Leu Ala Glu Lys Lys Glu Val Tyr Lys Asp
        275                 280                 285

Val Asp His Thr Ala Thr Tyr Met Ser Lys Met Glu Glu Ile Ser Arg
    290                 295                 300

Ile Ala Tyr Gln Asp Arg Lys Lys Asn Leu Gly Asp Pro Asn Tyr Val
305                 310                 315                 320

Asn Met Asp Pro Asn Lys Met Val Ser Asp Lys Tyr Ile Ser Thr Met
                325                 330                 335

Lys Asn Glu Asn Gly Asp Ala Leu Ser Glu Ala Glu His Glu Ser Thr
            340                 345                 350

Thr His Phe Val Ile Ile Asp Arg Asp Gly Thr Val Val Ser Ser Thr
        355                 360                 365

Asn Thr Leu Ser Asn Phe Phe Gly Thr Gly Lys Tyr Thr Ala Gly Phe
    370                 375                 380

Phe Leu Asn Asn Gln Leu Gln Asn Phe Gly Ser Glu Gly Phe Asn Ser
385                 390                 395                 400

Tyr Glu Pro Gly Lys Arg Ser Arg Thr Phe Met Ala Pro Thr Val Leu
                405                 410                 415

Lys Lys Asp Gly Glu Thr Ile Gly Ile Gly Ser Pro Gly Gly Asn Arg
            420                 425                 430

Ile Pro Gln Ile Leu Thr Pro Ile Leu Asp Lys Tyr Thr His Gly Lys
        435                 440                 445

Gly Ser Leu Gln Asp Ile Ile Asn Glu Tyr Arg Phe Thr Phe Glu Lys
    450                 455                 460

Asn Thr Ala Tyr Thr Glu Ile Gln Leu Ser Ser Glu Val Lys Asn Glu
465                 470                 475                 480

Leu Ser Arg Lys Gly Leu Asn Val Lys Lys Lys Val Ser Pro Ala Phe
                485                 490                 495

Phe Gly Gly Val Gln Ala Leu Ile Lys Asp Glu Arg Asp Asn Val Ile
            500                 505                 510

Thr Gly Ala Gly Asp Gly Arg Arg Asn Gly Thr Trp Lys Ser Asn Lys
        515                 520                 525


<210> SEQ ID NO 2
<211> LENGTH: 504
<212> TYPE: PRT
<213> ORGANISM: Artificial Sequence
<220> FEATURE:
<223> OTHER INFORMATION: synthetic construct

<400> SEQUENCE: 2

Met Thr Thr His Phe Val Ile Ile Asp Arg Asp Gly Thr Val Val Ser
1               5                   10                  15

Ser Thr Asn Thr Leu Ser Asn Phe Phe Gly Thr Gly Lys Tyr Thr Ala
            20                  25                  30

Gly Phe Phe Leu Asn Asn Gln Leu Gln Asn Phe Gly Ser Glu Gly Phe
        35                  40                  45

Asn Ser Tyr Glu Pro Gly Lys Arg Ser Arg Thr Phe Met Ala Pro Thr
    50                  55                  60

Val Leu Lys Lys Asp Gly Glu Thr Ile Gly Ile Gly Ser Pro Gly Gly
65                  70                  75                  80
```

-continued

```
Asn Arg Ile Pro Gln Ile Leu Thr Pro Ile Leu Asp Lys Tyr Thr His
                85                  90                  95

Gly Lys Gly Ser Leu Gln Asp Ile Ile Asn Glu Tyr Arg Phe Thr Phe
            100                 105                 110

Glu Lys Asn Thr Ala Tyr Thr Glu Ile Gln Leu Ser Ser Glu Val Lys
        115                 120                 125

Asn Glu Leu Ser Arg Lys Gly Leu Asn Val Lys Lys Lys Val Ser Pro
    130                 135                 140

Ala Phe Phe Gly Gly Val Gln Ala Leu Ile Lys Asp Glu Arg Asp Asn
145                 150                 155                 160

Val Ile Thr Gly Ala Gly Asp Gly Arg Arg Asn Gly Thr Trp Lys Ser
                165                 170                 175

Gly Gly Ser Gly Thr Tyr Gly Val Ser Ala Ser His Pro Leu Ala Val
            180                 185                 190

Glu Glu Gly Met Lys Val Leu Lys Asn Gly Gly Ser Ala Val Asp Ala
        195                 200                 205

Ala Ile Val Val Ser Tyr Val Leu Gly Val Val Glu Leu His Ala Ser
    210                 215                 220

Gly Ile Gly Gly Gly Gly Gly Met Leu Ile Ile Ser Lys Asp Lys Glu
225                 230                 235                 240

Thr Phe Ile Asp Tyr Arg Glu Thr Thr Pro Tyr Phe Thr Gly Asn Gln
                245                 250                 255

Lys Pro His Ile Gly Val Pro Gly Phe Val Ala Gly Met Glu Tyr Ile
            260                 265                 270

His Asp Asn Tyr Gly Ser Leu Pro Met Gly Glu Leu Leu Gln Pro Ala
        275                 280                 285

Ile Asn Tyr Ala Glu Lys Gly Phe Lys Val Asp Asp Ser Leu Thr Met
    290                 295                 300

Arg Leu Asp Leu Ala Lys Pro Arg Ile Tyr Ser Asp Lys Leu Ser Ile
305                 310                 315                 320

Phe Tyr Pro Asn Gly Glu Pro Ile Glu Thr Gly Glu Thr Leu Ile Gln
                325                 330                 335

Thr Asp Leu Ala Arg Thr Leu Lys Lys Ile Gln Lys Glu Gly Ala Lys
            340                 345                 350

Gly Phe Tyr Glu Gly Gly Val Ala Arg Ala Ile Ser Lys Thr Ala Lys
        355                 360                 365

Ile Ser Leu Glu Asp Ile Lys Gly Tyr Lys Val Glu Val Arg Lys Pro
    370                 375                 380

Val Lys Gly Asn Tyr Met Gly Tyr Asp Val Tyr Thr Ala Pro Pro Pro
385                 390                 395                 400

Phe Ser Gly Val Thr Leu Leu Gln Met Leu Lys Leu Ala Glu Lys Lys
                405                 410                 415

Glu Val Tyr Lys Asp Val Asp His Thr Ala Thr Tyr Met Ser Lys Met
            420                 425                 430

Glu Glu Ile Ser Arg Ile Ala Tyr Gln Asp Arg Lys Lys Asn Leu Gly
        435                 440                 445

Asp Pro Asn Tyr Val Asn Met Asp Pro Asn Lys Met Val Ser Asp Lys
    450                 455                 460

Tyr Ile Cys Thr Met Lys Asn Glu Asn Gly Asp Ala Leu Ser Glu Ala
465                 470                 475                 480

Glu His Glu Ser Gly Ser Thr Glu Asn Leu Tyr Phe Gln Ser Gly Ala
                485                 490                 495

Leu Glu His His His His His His
```

-continued

500

<210> SEQ ID NO 3
<211> LENGTH: 499
<212> TYPE: PRT
<213> ORGANISM: Artificial Sequence
<220> FEATURE:
<223> OTHER INFORMATION: synthetic construct

<400> SEQUENCE: 3

Met Thr Thr His Phe Val Ile Ile Asp Arg Asp Gly Thr Val Val Ser
1 5 10 15

Ser Thr Asn Thr Leu Ser Asn Phe Phe Gly Thr Gly Lys Tyr Thr Ala
20 25 30

Gly Phe Phe Leu Asn Asn Gln Leu Gln Asn Phe Gly Ser Glu Gly Phe
35 40 45

Asn Ser Tyr Glu Pro Gly Lys Arg Ser Arg Thr Phe Met Ala Pro Thr
50 55 60

Val Leu Lys Lys Asp Gly Glu Thr Ile Gly Ile Gly Ser Pro Gly Gly
65 70 75 80

Asn Arg Ile Pro Gln Ile Leu Thr Pro Ile Leu Asp Lys Tyr Thr His
85 90 95

Gly Lys Gly Ser Leu Gln Asp Ile Ile Asn Glu Tyr Arg Phe Thr Phe
100 105 110

Glu Lys Asn Thr Ala Tyr Thr Glu Ile Gln Leu Ser Ser Glu Val Lys
115 120 125

Asn Glu Leu Ser Arg Lys Gly Leu Asn Val Lys Lys Lys Val Ser Pro
130 135 140

Ala Phe Phe Gly Gly Val Gln Ala Leu Ile Lys Asp Glu Arg Asp Asn
145 150 155 160

Val Ile Thr Gly Ala Gly Asp Gly Arg Arg Asn Gly Thr Trp Lys Ser
165 170 175

Gly Gly Ser Gly Thr Tyr Gly Val Ser Ala Ser His Pro Leu Ala Val
180 185 190

Glu Glu Gly Met Lys Val Leu Lys Asn Gly Gly Ser Ala Val Asp Ala
195 200 205

Ala Ile Val Val Ser Tyr Val Leu Gly Val Val Glu Leu His Ala Ser
210 215 220

Gly Ile Gly Gly Gly Gly Gly Met Leu Ile Ile Ser Lys Asp Lys Glu
225 230 235 240

Thr Phe Ile Asp Tyr Arg Glu Thr Thr Pro Tyr Phe Thr Gly Asn Gln
245 250 255

Lys Pro His Ile Gly Val Pro Gly Phe Val Ala Gly Met Glu Tyr Ile
260 265 270

His Asp Asn Tyr Gly Ser Leu Pro Met Gly Glu Leu Leu Gln Pro Ala
275 280 285

Ile Asn Tyr Ala Glu Lys Gly Phe Lys Val Asp Asp Ser Leu Thr Met
290 295 300

Arg Leu Asp Leu Ala Lys Pro Arg Ile Tyr Ser Asp Lys Leu Ser Ile
305 310 315 320

Phe Tyr Pro Asn Gly Glu Pro Ile Glu Thr Gly Glu Thr Leu Ile Gln
325 330 335

Thr Asp Leu Ala Arg Thr Leu Lys Lys Ile Gln Lys Glu Gly Ala Lys
340 345 350

Gly Phe Tyr Glu Gly Gly Val Ala Arg Ala Ile Ser Lys Thr Ala Lys

-continued

```
        355                 360                 365

Ile Ser Leu Glu Asp Ile Lys Gly Tyr Lys Val Glu Val Arg Lys Pro
    370                 375                 380

Val Lys Gly Asn Tyr Met Gly Tyr Asp Val Tyr Thr Ala Pro Pro Pro
385                 390                 395                 400

Phe Ser Gly Val Thr Leu Leu Gln Met Leu Lys Leu Ala Glu Lys Lys
                405                 410                 415

Glu Val Tyr Lys Asp Val Asp His Thr Ala Thr Tyr Met Ser Lys Met
            420                 425                 430

Glu Glu Ile Ser Arg Ile Ala Tyr Gln Asp Arg Lys Lys Asn Leu Gly
        435                 440                 445

Asp Pro Asn Tyr Val Asn Met Asp Pro Asn Lys Met Val Ser Asp Lys
    450                 455                 460

Tyr Ile Cys Thr Met Lys Asn Glu Asn Gly Asp Ala Leu Ser Glu Ala
465                 470                 475                 480

Glu His Glu Ser Ile Glu Gly Arg Val Ser Leu Glu His His His His
                485                 490                 495

His His His


<210> SEQ ID NO 4
<211> LENGTH: 732
<212> TYPE: PRT
<213> ORGANISM: Artificial Sequence
<220> FEATURE:
<223> OTHER INFORMATION: synthetic construct

<400> SEQUENCE: 4

Met Thr Thr His Phe Val Ile Ile Asp Arg Asp Gly Thr Val Val Ser
1               5                   10                  15

Ser Thr Asn Thr Leu Ser Asn Phe Phe Gly Thr Gly Lys Tyr Thr Ala
            20                  25                  30

Gly Phe Phe Leu Asn Asn Gln Leu Gln Asn Phe Gly Ser Glu Gly Phe
        35                  40                  45

Asn Ser Tyr Glu Pro Gly Lys Arg Ser Arg Thr Phe Met Ala Pro Thr
    50                  55                  60

Val Leu Lys Lys Asp Gly Glu Thr Ile Gly Ile Gly Ser Pro Gly Gly
65                  70                  75                  80

Asn Arg Ile Pro Gln Ile Leu Thr Pro Ile Leu Asp Lys Tyr Thr His
                85                  90                  95

Gly Lys Gly Ser Leu Gln Asp Ile Ile Asn Glu Tyr Arg Phe Thr Phe
            100                 105                 110

Glu Lys Asn Thr Ala Tyr Thr Glu Ile Gln Leu Ser Ser Glu Val Lys
        115                 120                 125

Asn Glu Leu Ser Arg Lys Gly Leu Asn Val Lys Lys Lys Val Ser Pro
    130                 135                 140

Ala Phe Phe Gly Gly Val Gln Ala Leu Ile Lys Asp Glu Arg Asp Asn
145                 150                 155                 160

Val Ile Thr Gly Ala Gly Asp Gly Arg Arg Asn Gly Thr Trp Lys Ser
                165                 170                 175

Gly Gly Ser Gly Thr Tyr Gly Val Ser Ala Ser His Pro Leu Ala Val
            180                 185                 190

Glu Glu Gly Met Lys Val Leu Lys Asn Gly Gly Ser Ala Val Asp Ala
        195                 200                 205

Ala Ile Val Val Ser Tyr Val Leu Gly Val Val Glu Leu His Ala Ser
    210                 215                 220
```

-continued

```
Gly Ile Gly Gly Gly Gly Gly Met Leu Ile Ile Ser Lys Asp Lys Glu
225                 230                 235                 240

Thr Phe Ile Asp Tyr Arg Glu Thr Thr Pro Tyr Phe Thr Gly Asn Gln
                245                 250                 255

Lys Pro His Ile Gly Val Pro Gly Phe Val Ala Gly Met Glu Tyr Ile
            260                 265                 270

His Asp Asn Tyr Gly Ser Leu Pro Met Gly Glu Leu Leu Gln Pro Ala
        275                 280                 285

Ile Asn Tyr Ala Glu Lys Gly Phe Lys Val Asp Asp Ser Leu Thr Met
    290                 295                 300

Arg Leu Asp Leu Ala Lys Pro Arg Ile Tyr Ser Asp Lys Leu Ser Ile
305                 310                 315                 320

Phe Tyr Pro Asn Gly Glu Pro Ile Glu Thr Gly Glu Thr Leu Ile Gln
                325                 330                 335

Thr Asp Leu Ala Arg Thr Leu Lys Lys Ile Gln Lys Glu Gly Ala Lys
            340                 345                 350

Gly Phe Tyr Glu Gly Gly Val Ala Arg Ala Ile Ser Lys Thr Ala Lys
        355                 360                 365

Ile Ser Leu Glu Asp Ile Lys Gly Tyr Lys Val Glu Val Arg Lys Pro
    370                 375                 380

Val Lys Gly Asn Tyr Met Gly Tyr Asp Val Tyr Thr Ala Pro Pro Pro
385                 390                 395                 400

Phe Ser Gly Val Thr Leu Leu Gln Met Leu Lys Leu Ala Glu Lys Lys
                405                 410                 415

Glu Val Tyr Lys Asp Val Asp His Thr Ala Thr Tyr Met Ser Lys Met
            420                 425                 430

Glu Glu Ile Ser Arg Ile Ala Tyr Gln Asp Arg Lys Lys Asn Leu Gly
        435                 440                 445

Asp Pro Asn Tyr Val Asn Met Asp Pro Asn Lys Met Val Ser Asp Lys
    450                 455                 460

Tyr Ile Cys Thr Met Lys Asn Glu Asn Gly Asp Ala Leu Ser Glu Ala
465                 470                 475                 480

Glu His Glu Ser Gly Ser Gly Ala Lys Lys Ile Val Pro Arg Asp Cys
                485                 490                 495

Gly Cys Lys Pro Cys Ile Cys Thr Val Pro Glu Val Ser Ser Val Phe
            500                 505                 510

Ile Phe Pro Pro Lys Pro Lys Asp Val Leu Thr Ile Thr Leu Thr Pro
        515                 520                 525

Lys Val Thr Cys Val Val Val Asp Ile Ser Lys Asp Asp Pro Glu Val
    530                 535                 540

Gln Phe Ser Trp Phe Val Asp Asp Val Glu Val His Thr Ala Gln Thr
545                 550                 555                 560

Gln Pro Arg Glu Glu Gln Phe Asn Ser Thr Phe Arg Ser Val Ser Glu
                565                 570                 575

Leu Pro Ile Met His Gln Asp Trp Leu Asn Gly Lys Glu Phe Lys Cys
            580                 585                 590

Arg Val Asn Ser Ala Ala Phe Pro Ala Pro Ile Glu Lys Thr Ile Ser
        595                 600                 605

Lys Thr Lys Gly Arg Pro Lys Ala Pro Gln Val Tyr Thr Ile Pro Pro
    610                 615                 620

Pro Lys Glu Gln Met Ala Lys Asp Lys Val Ser Leu Thr Cys Met Ile
625                 630                 635                 640
```

-continued

```
Thr Asp Phe Phe Pro Glu Asp Ile Thr Val Glu Trp Gln Trp Asn Gly
                645                 650                 655

Gln Pro Ala Glu Asn Tyr Lys Asn Thr Gln Pro Ile Met Asp Thr Asp
            660                 665                 670

Gly Ser Tyr Phe Val Tyr Ser Lys Leu Asn Val Gln Lys Ser Asn Trp
        675                 680                 685

Glu Ala Gly Asn Thr Phe Thr Cys Ser Val Leu His Glu Gly Leu His
    690                 695                 700

Asn His His Thr Glu Lys Ser Leu Ser His Ser Pro Gly Lys Leu Gly
705                 710                 715                 720

Ile Glu Gly Arg Leu Glu His His His His His His
                725                 730


<210> SEQ ID NO 5
<211> LENGTH: 736
<212> TYPE: PRT
<213> ORGANISM: Artificial Sequence
<220> FEATURE:
<223> OTHER INFORMATION: synthetic construct

<400> SEQUENCE: 5

Met Thr Thr His Phe Val Ile Ile Asp Arg Asp Gly Thr Val Val Ser
1               5                   10                  15

Ser Thr Asn Thr Leu Ser Asn Phe Phe Gly Thr Gly Lys Tyr Thr Ala
            20                  25                  30

Gly Phe Phe Leu Asn Asn Gln Leu Gln Asn Phe Gly Ser Glu Gly Phe
        35                  40                  45

Asn Ser Tyr Glu Pro Gly Lys Arg Ser Arg Thr Phe Met Ala Pro Thr
    50                  55                  60

Val Leu Lys Lys Asp Gly Glu Thr Ile Gly Ile Gly Ser Pro Gly Gly
65                  70                  75                  80

Asn Arg Ile Pro Gln Ile Leu Thr Pro Ile Leu Asp Lys Tyr Thr His
                85                  90                  95

Gly Lys Gly Ser Leu Gln Asp Ile Ile Asn Glu Tyr Arg Phe Thr Phe
            100                 105                 110

Glu Lys Asn Thr Ala Tyr Thr Glu Ile Gln Leu Ser Ser Glu Val Lys
        115                 120                 125

Asn Glu Leu Ser Arg Lys Gly Leu Asn Val Lys Lys Lys Val Ser Pro
    130                 135                 140

Ala Phe Phe Gly Gly Val Gln Ala Leu Ile Lys Asp Glu Arg Asp Asn
145                 150                 155                 160

Val Ile Thr Gly Ala Gly Asp Gly Arg Arg Asn Gly Thr Trp Lys Ser
                165                 170                 175

Gly Gly Ser Gly Thr Tyr Gly Val Ser Ala Ser His Pro Leu Ala Val
            180                 185                 190

Glu Glu Gly Met Lys Val Leu Lys Asn Gly Gly Ser Ala Val Asp Ala
        195                 200                 205

Ala Ile Val Val Ser Tyr Val Leu Gly Val Val Glu Leu His Ala Ser
    210                 215                 220

Gly Ile Gly Gly Gly Gly Gly Met Leu Ile Ile Ser Lys Asp Lys Glu
225                 230                 235                 240

Thr Phe Ile Asp Tyr Arg Glu Thr Thr Pro Tyr Phe Thr Gly Asn Gln
                245                 250                 255

Lys Pro His Ile Gly Val Pro Gly Phe Val Ala Gly Met Glu Tyr Ile
            260                 265                 270
```

-continued

```
His Asp Asn Tyr Gly Ser Leu Pro Met Gly Glu Leu Leu Gln Pro Ala
        275                 280                 285

Ile Asn Tyr Ala Glu Lys Gly Phe Lys Val Asp Asp Ser Leu Thr Met
    290                 295                 300

Arg Leu Asp Leu Ala Lys Pro Arg Ile Tyr Ser Asp Lys Leu Ser Ile
305                 310                 315                 320

Phe Tyr Pro Asn Gly Glu Pro Ile Glu Thr Gly Glu Thr Leu Ile Gln
                325                 330                 335

Thr Asp Leu Ala Arg Thr Leu Lys Lys Ile Gln Lys Glu Gly Ala Lys
            340                 345                 350

Gly Phe Tyr Glu Gly Gly Val Ala Arg Ala Ile Ser Lys Thr Ala Lys
        355                 360                 365

Ile Ser Leu Glu Asp Ile Lys Gly Tyr Lys Val Glu Val Arg Lys Pro
    370                 375                 380

Val Lys Gly Asn Tyr Met Gly Tyr Asp Val Tyr Thr Ala Pro Pro Pro
385                 390                 395                 400

Phe Ser Gly Val Thr Leu Leu Gln Met Leu Lys Leu Ala Glu Lys Lys
                405                 410                 415

Glu Val Tyr Lys Asp Val Asp His Thr Ala Thr Tyr Met Ser Lys Met
            420                 425                 430

Glu Glu Ile Ser Arg Ile Ala Tyr Gln Asp Arg Lys Lys Asn Leu Gly
        435                 440                 445

Asp Pro Asn Tyr Val Asn Met Asp Pro Asn Lys Met Val Ser Asp Lys
    450                 455                 460

Tyr Ile Cys Thr Met Lys Asn Glu Asn Gly Asp Ala Leu Ser Glu Ala
465                 470                 475                 480

Glu His Glu Ser Gly Ser Gly Ala Lys Lys Ile Val Pro Arg Asp Cys
                485                 490                 495

Gly Cys Lys Pro Cys Ile Cys Thr Val Pro Glu Val Ser Ser Val Phe
            500                 505                 510

Ile Phe Pro Pro Lys Pro Lys Asp Val Leu Thr Ile Thr Leu Thr Pro
        515                 520                 525

Lys Val Thr Cys Val Val Val Asp Ile Ser Lys Asp Asp Pro Glu Val
    530                 535                 540

Gln Phe Ser Trp Phe Val Asp Asp Val Glu Val His Thr Ala Gln Thr
545                 550                 555                 560

Gln Pro Arg Glu Glu Gln Phe Asn Ser Thr Phe Arg Ser Val Ser Glu
                565                 570                 575

Leu Pro Ile Met His Gln Asp Trp Leu Asn Gly Lys Glu Phe Lys Cys
            580                 585                 590

Arg Val Asn Ser Ala Ala Phe Pro Ala Pro Ile Glu Lys Thr Ile Ser
        595                 600                 605

Lys Thr Lys Gly Arg Pro Lys Ala Pro Gln Val Tyr Thr Ile Pro Pro
    610                 615                 620

Pro Lys Glu Gln Met Ala Lys Asp Lys Val Ser Leu Thr Cys Met Ile
625                 630                 635                 640

Thr Asp Phe Phe Pro Glu Asp Ile Thr Val Glu Trp Gln Trp Asn Gly
                645                 650                 655

Gln Pro Ala Glu Asn Tyr Lys Asn Thr Gln Pro Ile Met Asp Thr Asp
            660                 665                 670

Gly Ser Tyr Phe Val Tyr Ser Lys Leu Asn Val Gln Lys Ser Asn Trp
        675                 680                 685

Glu Ala Gly Asn Thr Phe Thr Cys Ser Val Leu His Glu Gly Leu His
```

-continued

| | | | | | | | | | | | | | | | |
|---|---|---|---|---|---|---|---|---|---|---|---|---|---|---|---|
| | 690 | | | | | 695 | | | | | 700 | | | | |
| Asn | His | His | Thr | Glu | Lys | Ser | Leu | Ser | His | Ser | Pro | Gly | Lys | Leu | Gly |
| 705 | | | | | 710 | | | | | 715 | | | | | 720 |
| Ile | Glu | Gly | Arg | Gly | Ser | Ser | Gly | Leu | Glu | His | His | His | His | His | His |
| | | | | 725 | | | | | 730 | | | | | 735 | |